(12) United States Patent
Hashimoto et al.

(10) Patent No.: US 10,114,064 B2
(45) Date of Patent: Oct. 30, 2018

(54) ERROR DETECTION DEVICE

(71) Applicant: Panasonic Intellectual Property Management Co., Ltd., Osaka (JP)

(72) Inventors: Daichi Hashimoto, Saitama (JP); Takashi Nakazawa, Kanagawa (JP); Haruhiko Sekino, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/516,425

(22) PCT Filed: Oct. 23, 2015

(86) PCT No.: PCT/JP2015/005337
§ 371 (c)(1),
(2) Date: Apr. 3, 2017

(87) PCT Pub. No.: WO2016/067576
PCT Pub. Date: May 6, 2016

(65) Prior Publication Data
US 2017/0299648 A1 Oct. 19, 2017

(30) Foreign Application Priority Data
Oct. 31, 2014 (JP) .................. 2014-223266

(51) Int. Cl.
*G01R 1/00* (2006.01)
*G01R 31/12* (2006.01)
(Continued)

(52) U.S. Cl.
CPC ........ *G01R 31/1272* (2013.01); *B60L 3/0069* (2013.01); *G01R 31/025* (2013.01);
(Continued)

(58) Field of Classification Search
CPC .......... G01R 1/00; H04B 1/00; H04B 2201/00
See application file for complete search history.

(56) References Cited

U.S. PATENT DOCUMENTS

2002/0063474 A1* 5/2002 Wasaki ............... H04B 3/56
307/89
2002/0167303 A1* 11/2002 Nakano .............. G01R 15/16
324/126
(Continued)

FOREIGN PATENT DOCUMENTS

| JP | 2005-114497 A | 4/2005 |
|---|---|---|
| JP | 3781289 B | 5/2006 |

(Continued)

OTHER PUBLICATIONS

The Extended European Search Report dated Nov. 7, 2017 for the related European Patent Application No. 15855470.9.
(Continued)

*Primary Examiner* — Jermele M Hollington
*Assistant Examiner* — Temilade Rhodes-Vivour
(74) *Attorney, Agent, or Firm* — Pearne & Gordon LLP

(57) ABSTRACT

An abnormality detection device includes: a coupling-capacitor having a first-end and a second-end coupled with a high-voltage circuit; a signal output unit; a signal extraction unit; and a signal input unit. The signal output unit is coupled with the first-end of the coupling-capacitor via a detection-resistor, and outputs an alternating-current inspection-signal. The signal extraction unit extracts the inspection-signal, as an extraction-signal, output between the detection-resistor and the coupling-capacitor. The signal input unit detects abnormality of insulation resistance of the high-voltage circuit based on a level of the inputted extraction-signal. The signal extraction unit includes a signal removing filter and a subtraction circuit. The filter removes a signal equal in frequency to the inspection-signal and (Continued)

passes low-frequency noises lower in frequency than the inspection-signal. The subtraction circuit outputs a differential signal, as the extraction-signal, between a signal having passed through the filter and a signal not having passed through the filter.

4 Claims, 7 Drawing Sheets

(51) Int. Cl.
*G01R 31/317* (2006.01)
*B60L 3/00* (2006.01)
*G01R 31/02* (2006.01)
*G01N 1/00* (2006.01)
*H04B 3/56* (2006.01)
*G01R 27/18* (2006.01)
*G01R 31/00* (2006.01)

(52) U.S. Cl.
CPC ......... *G01R 31/31706* (2013.01); *G01N 1/00* (2013.01); *G01N 2201/00* (2013.01); *G01R 1/00* (2013.01); *G01R 27/18* (2013.01); *G01R 31/006* (2013.01); *H04B 3/56* (2013.01)

(56) References Cited

U.S. PATENT DOCUMENTS

| 2005/0073320 | A1 | 4/2005 | Yamamoto et al. |
| 2009/0134881 | A1 | 5/2009 | Tachizaki |
| 2009/0319210 | A1* | 12/2009 | Yanagisawa ........... G01R 15/16 702/64 |
| 2013/0245869 | A1* | 9/2013 | Nishida ................. B60L 3/0069 701/22 |
| 2014/0197683 | A1 | 7/2014 | Migita et al. |
| 2015/0042405 | A1* | 2/2015 | Kim ..................... H03G 3/3042 330/279 |

FOREIGN PATENT DOCUMENTS

| JP | 2007-187454 A | 7/2007 |
| JP | 2008-097743 A | 4/2008 |
| JP | 2013-032977 A | 2/2013 |

OTHER PUBLICATIONS

Martin Everts: "Band-Pass Filters", Mar. 7, 2007, pp. 1-25, XP055419720.
International Search Report of PCT application No. PCT/JP2015/005337 dated Dec. 15, 2015.

* cited by examiner

ERROR DETECTION DEVICE

TECHNICAL FIELD

The present invention relates to abnormality detection devices for detecting abnormalities of insulation resistance of high-voltage circuits.

BACKGROUND ART

Abnormality detection devices have previously been proposed which can detect abnormalities of insulation resistance of high-voltage circuits. Patent Literature 1 discloses a ground-fault detection circuit, as an abnormality detection device, used in an electric vehicle. The ground-fault detection circuit disclosed in Patent Literature 1 includes: a coupling capacitor, an oscillator circuit unit, and a ground-fault detection circuit unit. The coupling capacitor has one end that is coupled with a high-voltage circuit. The oscillator circuit unit outputs an oscillation signal to the other end of the coupling capacitor via impedance. The ground-fault detection circuit unit determines occurrence of grounding of the high-voltage circuit on the basis of the amplitude of a signal between the impedance and the coupling capacitor.

In accordance with the ground-fault detection circuit disclosed in Patent Literature 1, the oscillation signal that is output from the oscillator circuit unit can be detected by the ground-fault detection circuit unit without a large voltage drop, as long as insulation resistance of the high-voltage circuit is normally held. On the other hand, if a ground fault develops in the high-voltage circuit, the oscillation signal that is output from the oscillator circuit unit exhibits a large voltage drop due to an electric current that flows from the high-voltage circuit to a ground point. The ground-fault detection circuit unit detects the voltage drop. This configuration makes it possible to determine whether or not a ground fault develops in the high-voltage circuit.

Moreover, the ground-fault detection circuit disclosed in Patent Literature 1 is equipped with either a band-pass filter or a high-pass filter between the ground-fault detection circuit unit and the coupling capacitor. The filter interrupts low-frequency noises generated in the high-voltage circuit. Unless the low-frequency noises are interrupted, the oscillation signal from the oscillator circuit unit is added with the low-frequency noises, then is inputted to the ground-fault detection circuit unit. For this reason, the thus-inputted signal may exceed a dynamic range of the ground-fault detection circuit unit. In this case, a part of the signal inputted to the ground-fault detection circuit unit is unfavorably clipped off, making it difficult to correctly detect ground faults. Fortunately, the presence of either the band-pass or high-pass filter described above allows avoidance of such a signal clipping.

CITATION LIST

Patent Literature

PTL 1: Japanese Patent No. 3781289

SUMMARY OF THE INVENTION

The present invention provides an abnormality detection device for detecting an abnormality of insulation resistance of a high-voltage circuit. The abnormality detection device is used to be coupled with the high-voltage circuit via a coupling capacitor. The abnormality detection device is capable of reducing influence of low-frequency noises from the high-voltage circuit and of eliminating the need for a filter circuit that has an expensive input capacitor for extracting an inspection signal.

The abnormality detection device according to one aspect of the present invention includes: a coupling capacitor having a first end and a second end that is to be coupled with the high-voltage circuit, a signal output unit, a signal extraction unit, and a signal input unit. The signal output unit is coupled with the first end of the coupling capacitor via a detection resistor, and outputs an alternating-current inspection signal. The signal extraction unit extracts the inspection signal as an extraction signal. The inspection signal is output between the detection resistor and the coupling capacitor. The signal input unit detects the abnormality of insulation resistance of the high-voltage circuit based on a level of the extraction signal that is inputted to the signal input unit. The signal extraction unit includes a signal removing filter and a subtraction circuit. The signal removing filter removes a signal equal in frequency to the inspection signal, and passes, through the filter, noises lower in frequency than the inspection signal. The subtraction circuit outputs a differential signal as the extraction signal. The differential signal is a difference between a signal having been passed through the signal removing filter and a signal not having been passed through the signal removing filter.

In accordance with the present invention, the influence of low-frequency noises from the high-voltage circuit can be reduced, and the need for a filter circuit having an expensive input capacitor for extracting the inspection signal can be eliminated.

DESCRIPTION OF EMBODIMENTS

Figure 1:
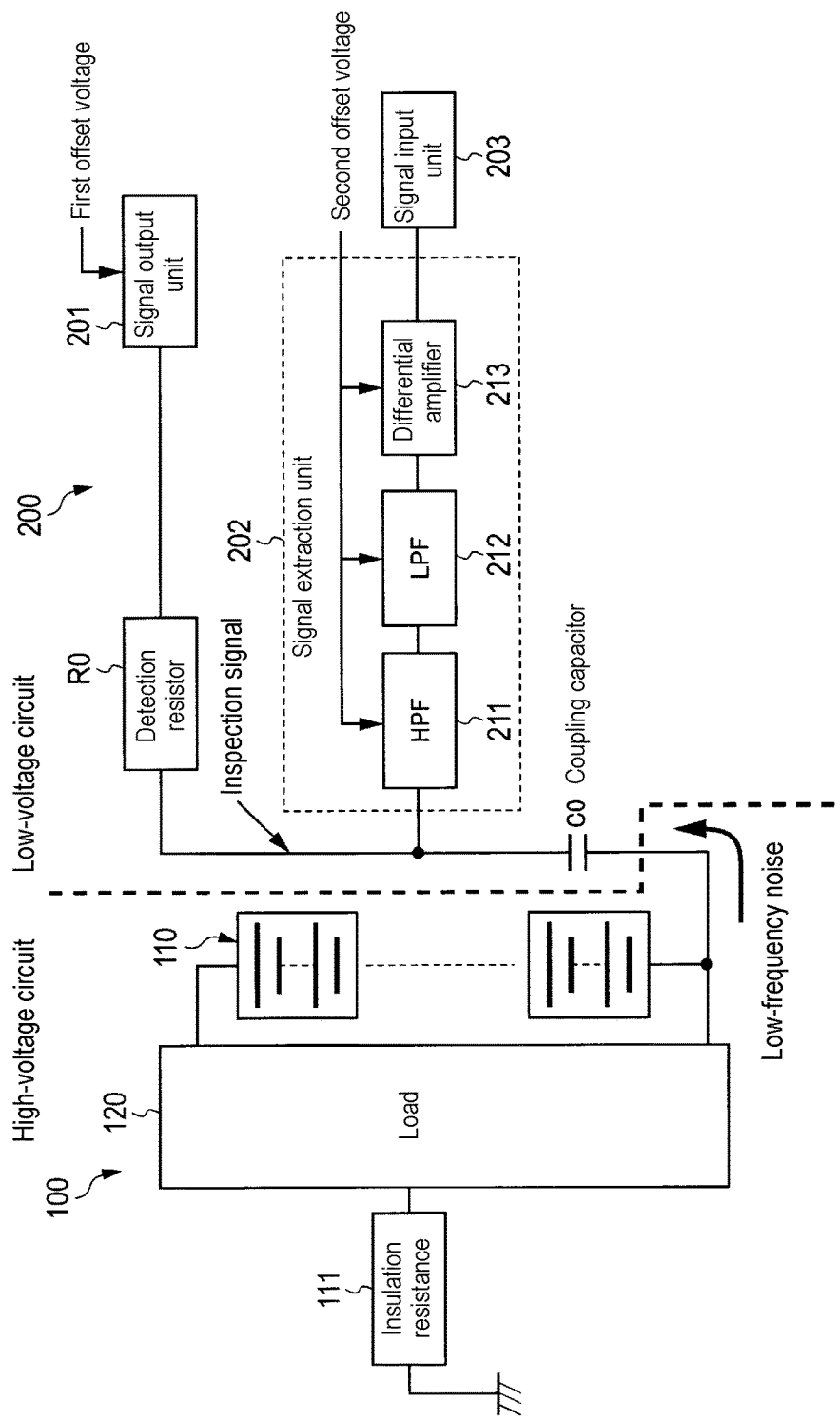
FIG. 1 is a configuration diagram of an abnormality detection device in a Comparative Example.

Prior to descriptions of embodiments of the present invention, problems faced by conventional technologies will be briefly described. FIG. 1 shows abnormality detection device 200 in a Comparative Example, to which the configuration of the ground-fault detection circuit disclosed in Patent Literature 1 is applied. Abnormality detection device 200 includes: coupling capacitor C0 having one end coupled with high-voltage circuit 100; detection resistor R0; signal output unit 201; signal extraction unit 202; and signal input unit 203. High-voltage circuit 100 includes: battery 110 for supplying a high voltage, and load 120 driven by the high voltage. High-voltage circuit 100, when being normally operated, is isolated from the ground via high insulation resistance 111.

Signal output unit 201 of abnormality detection device 200 outputs an alternating-current inspection signal to the other end of coupling capacitor C0 via detection resistor R0. Signal extraction unit 202 receives a signal at a node located midway between detection resistor R0 and the other end of coupling capacitor C0. Signal extraction unit 202 blocks low-frequency noises by high-pass filter (HPF) 211 and high-frequency noises by low-pass filter (LPF) 212, thereby extracting the signal having a frequency component of the inspection signal. Differential amplifier 213 amplifies the thus-extracted signal which has passed through both high-pass filter 211 and low-pass filter 212, and outputs the thus-amplified signal to signal input unit 203. Signal input unit 203 detects an abnormality of insulation resistance 111 of high-voltage circuit 100, based on a level of the thus-extracted signal.

As described above, the presence of high-pass filter 211 in signal extraction unit 202 can reduce influence of the low-frequency noises generated in high-voltage circuit 100, which can avoid the problem that the signal inputted to signal input unit 203 is unfavorably clipped off.

On the other hand, high-pass filter 211 requires an input capacitor. Such an input capacitor is required to have relatively large capacitance because high-pass filter 211 receives the inspection signal having a frequency not so high. Moreover, it is expected that a high voltage due to the abnormality of high-voltage circuit 100 will be applied on high-pass filter 211. For this reason, the input capacitor is required to have middle-and-high withstand voltage characteristics. Filling of these requirements concerning capacitance and withstand voltage results in an increase in component size and in cost of the input capacitor. Therefore, abnormality detection device 200 has faced the problems of an increased circuit area and increased component costs.

Hereinafter, the embodiments of the present invention will be described in detail with reference to the accompanying drawings.

First Exemplary Embodiment

Description of Configuration

Figure 2:
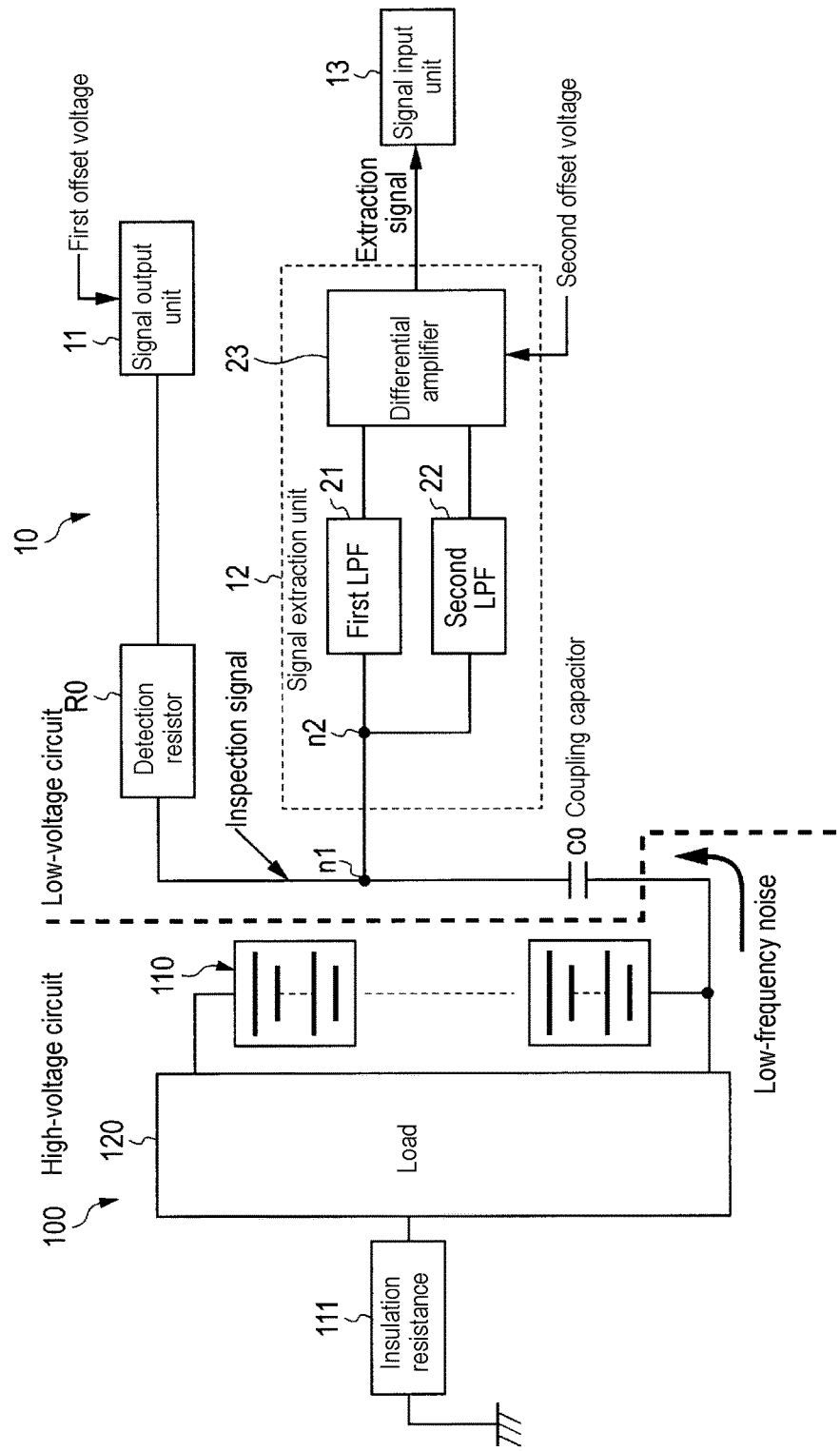
FIG. 2 is a configuration diagram of an abnormality detection device according to a first embodiment of the present invention.

FIG. 2 is a configuration diagram of abnormality detection device 10 according to a first embodiment of the present invention. Abnormality detection device 10 is mounted to a vehicle, for example, and serves as a device to detect an abnormality of insulation resistance 111 of high-voltage circuit 100. High-voltage circuit 100 includes battery 110 for supplying a high voltage and load 120 (e.g. a drive motor of an electric vehicle) driven by the high voltage. High-voltage circuit 100, when being normally operated, is isolated from the ground via high insulation resistance 111. In high-voltage circuit 100, low-frequency noises are generated at a frequency of which can be expected in advance.

Abnormality detection device 10 includes coupling capacitor C0, signal output unit 11, detection resistor R0, signal extraction unit 12, and signal input unit 13. Abnormality detection device 10 is supplied with low-voltage power (lower in voltage than a power supply for high-voltage circuit 100).

Coupling capacitor C0 couples abnormality detection device 10 to high-voltage circuit 100 in terms of an alternating current, and insulates high-voltage circuit 100 from abnormality detection device 10 in terms of a direct current. One end of coupling capacitor C0 is coupled with high-voltage circuit 100 (e.g. with the negative electrode of battery 110).

Signal output unit 11 outputs an alternating-current inspection signal. Signal output unit 11 is supplied with an offset voltage that is an intermediate voltage of the power supply voltage. Signal output unit 11 outputs an alternating-current voltage, as the inspection signal, with the alternating-current voltage varying around the offset voltage serving as a center. Signal output unit 11 outputs the inspection signal to the other end of coupling capacitor C0 via detection resistor R0.

Detection resistor R0 is a resistor that is intended to cause a voltage drop of the inspection signal when a current flows into high-voltage circuit 100 via coupling capacitor C0.

Signal extraction unit 12 extracts the inspection signal that is output to node n1 located midway between detection resistor R0 and coupling capacitor C0. Signal extraction unit 12 includes: first low-pass filter 21 (corresponding to a noise removing filter), second low-pass filter 22 (corresponding to a signal removing filter), and differential amplifier 23 (corresponding to a subtraction circuit). In the figures, each of the low-pass filters is abbreviated to LPF.

First low-pass filter 21 removes high-frequency noises having frequencies higher than that of the inspection signal, and passes the inspection signal and the low-frequency noises through first low-pass filter 21. The cutoff frequency of first low-pass filter 21 is set at a frequency higher than that of the inspection signal.

Second low-pass filter 22 removes the frequency component of the inspection signal, and passes the low-frequency noises lower in frequency than the inspection signal through second low-pass filter 22. The cutoff frequency of second low-pass filter 22 is set at a frequency between the frequency of the inspection signal and the frequencies of the low-frequency noises that are expected to be generated in high-voltage circuit 100.

Figure 3A:
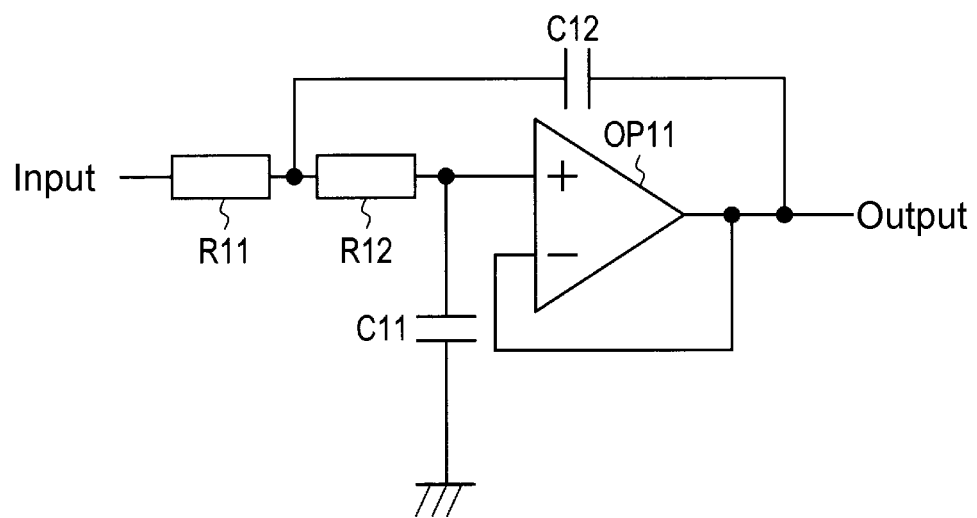
FIG. 3A is a circuit diagram of a first specific example of a low-pass filter.
Figure 3B:
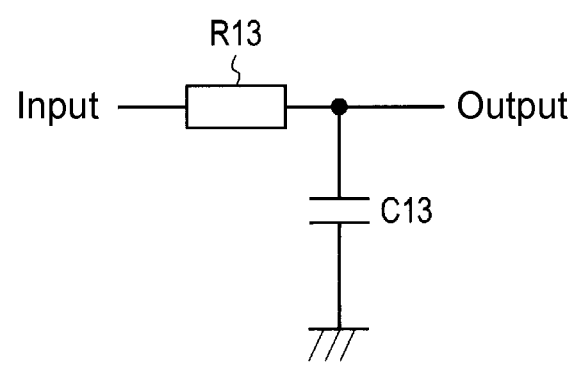
FIG. 3B is a circuit diagram of a second specific example of the low-pass filter.

Each of first low-pass filter 21 and second low-pass filter 22 may be configured as an active low-pass filter, as shown in FIG. 3A, that includes operational amplifier OP11, input resistors R11 and R12, and capacitors C11 and C12. First low-pass filter 21 may be configured as a passive low-pass filter, as shown in FIG. 3B, that includes input resistor R13 disposed in the signal line and capacitor C13 coupled between the signal line and the ground. None of first low-pass filter 21 and second low-pass filter 22 requires any input capacitor that has large capacitance and middle-and-high withstand voltage characteristics. Each of first low-pass filter 21 and second low-pass filter 22 has characteristics of not blocking direct-current components of the input signal. Accordingly, if a signal to which direct-current components have been added is inputted, this configuration allows each of these filters to pass the signal therethrough, as it contains the direct-current components, without the need for any offset voltage.

Differential amplifier 23 outputs a differential signal between an output of first low-pass filter 21 and an output of second low-pass filter 22, as an extraction signal extracted by signal extraction unit 12. Specifically, differential amplifier 23 amplifies the differential voltage between an output voltage of first low-pass filter 21 and an output voltage of second low-pass filter 22 with a predetermined amplification gain. Then, the differential amplifier outputs the thus-amplified differential signal. The amplification gain is set to be larger than 1 (one); however, it may be set to 1 (one) or smaller.

Signal input unit 13 receives the extraction signal from signal extraction unit 12. Specifically, signal input unit 13 is a microcomputer. The extraction signal received from signal extraction unit 12 is subjected to an analog-to-digital (A/D) conversion, then is inputted to signal input unit 13. Moreover, signal input unit 13 determines whether or not an abnormality of insulation resistance 111 is present by comparison between the level value of the extraction signal and a threshold value, for example.

Description of Operation

Figure 4A:
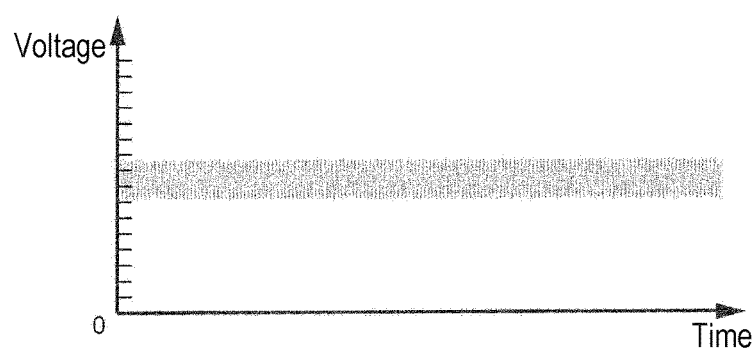
FIG. 4A is a waveform chart of an inspection signal that is output from a signal output unit of the abnormality detection device.
Figure 4B:
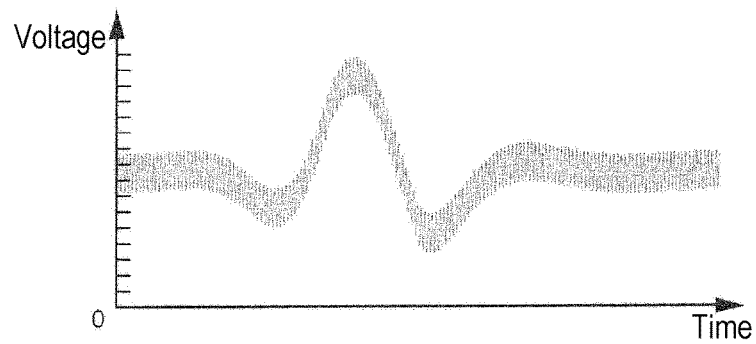
FIG. 4B is a waveform chart of a signal at node n1 of the abnormality detection device, with low-frequency noises having been added to the signal.
Figure 4C:
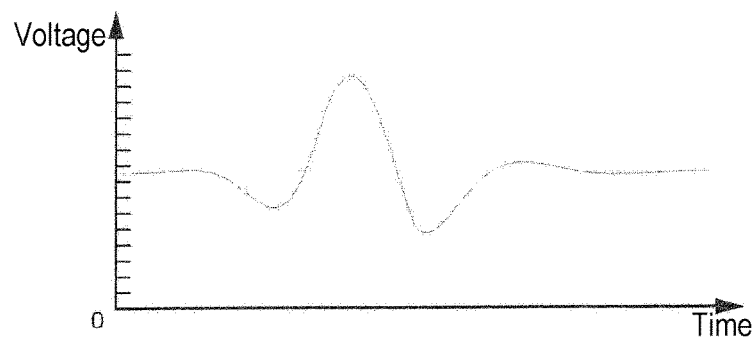
FIG. 4C is a waveform chart of an output signal from a second low-pass filter of the abnormality detection device.
Figure 4D:
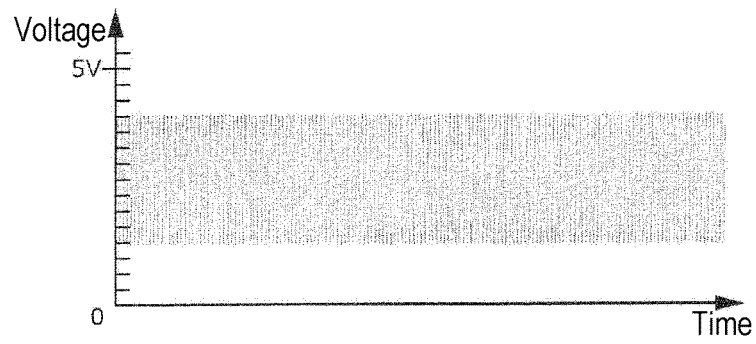
FIG. 4D is a waveform chart of an extraction signal that is output from a differential amplifier of the abnormality detection device.

FIGS. 4A to 4D show signals that are output to points in the abnormality detection device. FIG. 4A is a waveform chart of the inspection signal that is output from the signal output unit. FIG. 4B is a waveform chart of the signal at node n1, with low-frequency noises having been added to the signal. FIG. 4C is a waveform chart of an output signal from the second low-pass filter. FIG. 4D is a waveform chart of the extraction signal that is output from the differential amplifier.

As shown in FIG. 4A, signal output unit 11 outputs the alternating-current inspection signal that varies with a predetermined amplitude and frequency.

In high-voltage circuit 100, the low-frequency noises are generated which are lower in frequency than the inspection signal, as shown in FIG. 4C. When the low-frequency noises are generated, a signal which is a sum of the low-frequency noises and the inspection signal is output to node n1 that is located midway between detection resistor R0 and coupling capacitor C0, as shown in FIG. 4B. The sum signal is transferred to both first low-pass filter 21 and second low-pass filter 22.

First low-pass filter 21 removes the high-frequency noises that are higher in frequency than the inspection signal. When the signal shown in FIG. 4B is inputted, first low-pass filter 21 outputs a signal identical to the signal shown in FIG. 4B because the signal waveform shown in FIG. 4B does not contain any high-frequency noises.

Second low-pass filter 22 removes the frequency component of the inspection signal as shown in FIG. 4C, passes low-frequency components through it, and outputs the thus-passed signal.

As shown in FIG. 4D, differential amplifier 23 amplifies a differential signal between the output signal of first low-pass filter 21 and the output signal of second low-pass filter 22, with a predetermined amplification gain, and differential amplifier 23 outputs the thus-amplified signal as an extraction signal. Differential amplifier 23 is supplied with a predetermined offset voltage. With the predetermined offset voltage and the predetermined gain, the extraction signal which is output from differential amplifier 23 to signal input unit 13 is arranged to be within a dynamic range, e.g. from 0 (zero) V to 5 V, of signal input unit 13.

Signal input unit 13 receives the extraction signal from differential amplifier 23, and determines whether or not an abnormality of insulation resistance 111 of high-voltage circuit 100 is present, based on the level of the extraction signal. For example, when insulation resistance 111 is being held at a normal value, the amplitude of the extraction signal inputted to signal input unit 13 remains at a high level. On the other hand, if insulation resistance 111 decreases, a current associated with the inspection signal flows into the ground via coupling capacitor C0 and insulation resistance 111. This causes a voltage drop across detection resistor R0, resulting in a decrease in the level of the inspection signal at node n1. As a result, the level of amplitude of the inspection signal which is output from differential amplifier 23 to signal input unit 13 decreases, which allows signal input unit 13 to determine the abnormality of insulation resistance 111.

As described above, in accordance with abnormality detection device 10, signal extraction unit 12 does not require any filter circuit having an expensive input capacitor. Moreover, second low-pass filter 22 forms a signal by removing the frequency component of the inspection signal and by passing the low-frequency noises through second low-pass filter 22. Furthermore, differential amplifier 23 obtains a differential signal between the signal that has been passed through second low-pass filter 22 and the signal that has not been passed through second low-pass filter 22; the differential amplifier outputs the differential signal as an extraction signal. Such actions of second low-pass filter 22 and differential amplifier 23 can reduce the influence of the low-frequency noises on the extraction signal that is output from signal extraction unit 12 to signal input unit 13. Therefore, abnormality detection device 10 according to the first embodiment can reduce the influence of the low-frequency noises of high-voltage circuit 100, and eliminate the need for a filter circuit having an expensive capacitor for extracting the inspection signal.

Second Exemplary Embodiment

Figure 5:
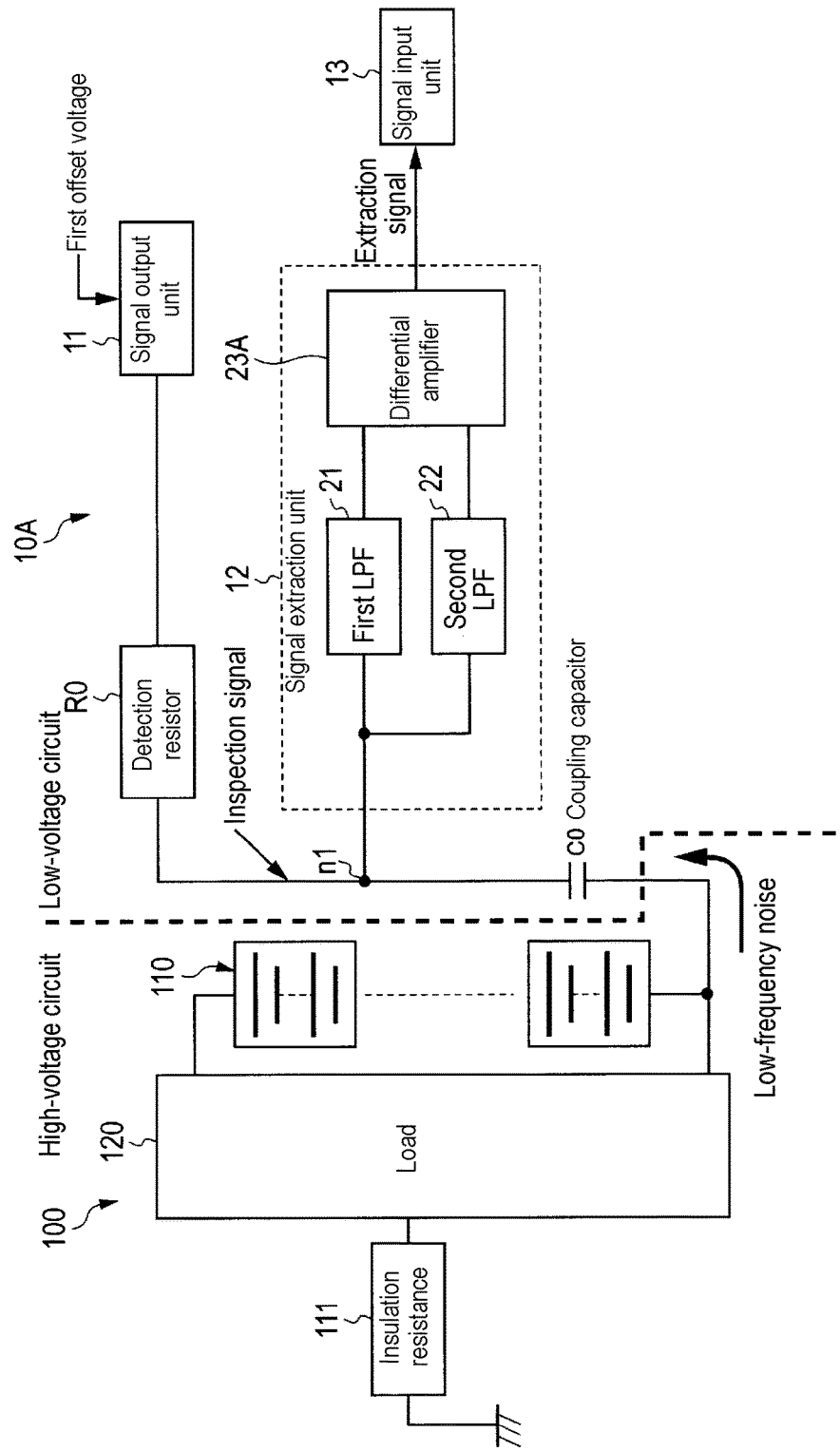
FIG. 5 is a configuration diagram of an abnormality detection device according to a second embodiment of the present invention.

FIG. 5 is a configuration diagram of abnormality detection device 10A according to a second embodiment. The configuration of abnormality detection device 10A is different from that according to the first embodiment in that differential amplifier 23A uses no offset voltage. The same configuration elements as those according to the first embodiment are designated by the same numerals and symbols as those in the first embodiment, and their detailed explanations are omitted.

Differential amplifier 23A amplifies a differential signal between a signal from first low-pass filter 21 and a signal from second low-pass filter 22, with a predetermined amplification gain, and outputs the thus-amplified differential signal as an extraction signal. Differential amplifier 23A is supplied with no offset voltage, so that differential amplifier 23A will output zero voltage if the voltage value of the differential signal obtained after subtraction is negative.

Signal input unit 13 receives, from differential amplifier 23A, an extraction signal in which waveforms not higher than 0 (zero) V have been clipped off. Signal input unit 13 measures the wave height of the extraction signal, and determines whether or not the abnormality of insulation resistance 111 is present, by comparison between the measured wave height value and a threshold value, for example.

The other operations are the same as those of abnormality detection device 10 described in the first embodiment.

As described above, in accordance with abnormality detection device 10A, differential amplifier 23A clips off the waveforms of not higher than 0 (zero) V of the extraction signal. Moreover, the need for supplying an offset voltage to signal extraction unit 12 is eliminated. Therefore, in addition to the same advantageous effects as those in the first embodiment, a reduction in the circuit area and in component costs can be achieved as a whole.

Third Exemplary Embodiment

Figure 6:
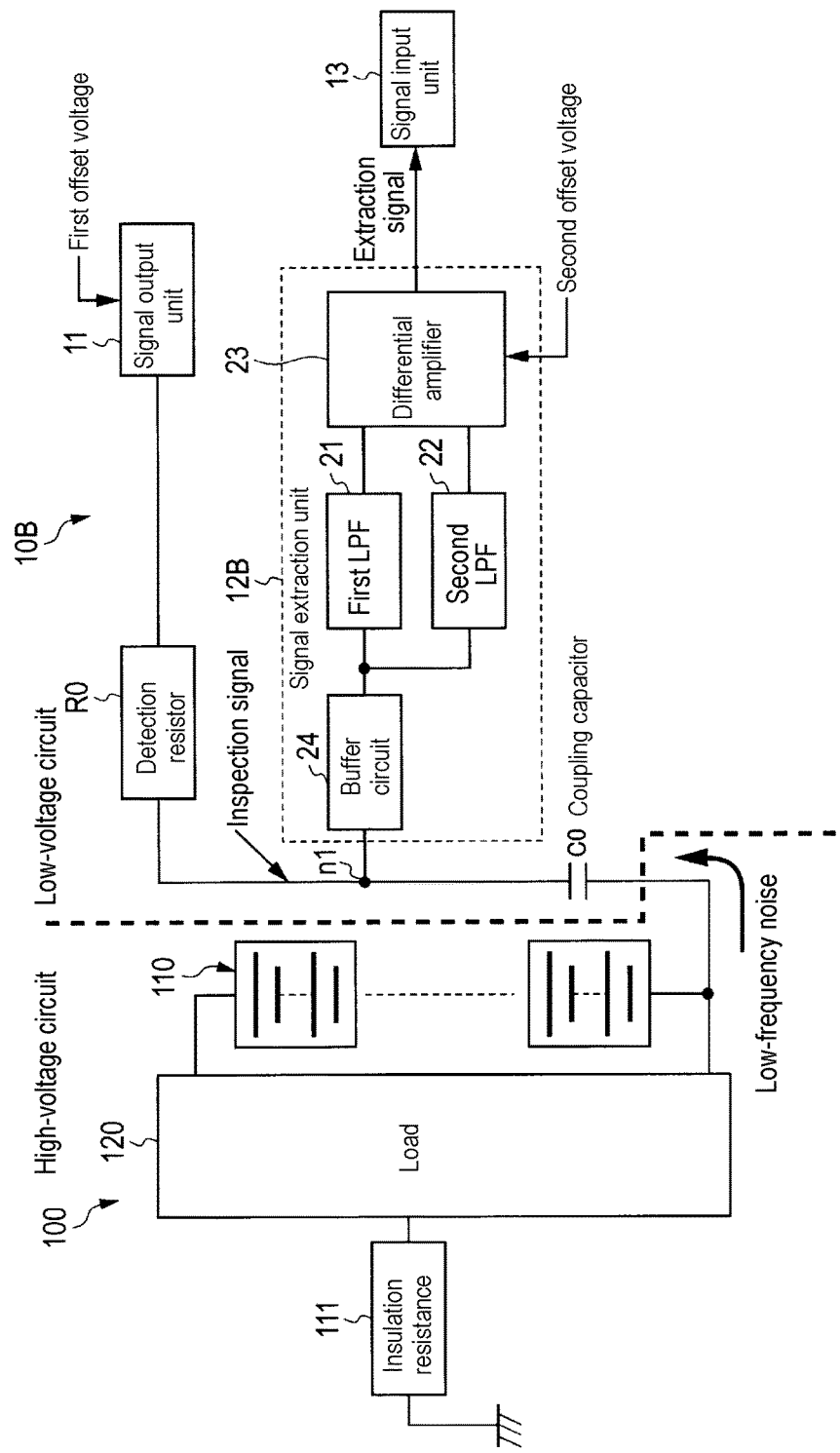
FIG. 6 is a configuration diagram of an abnormality detection device according to a third embodiment of the present invention.
Figure 7:
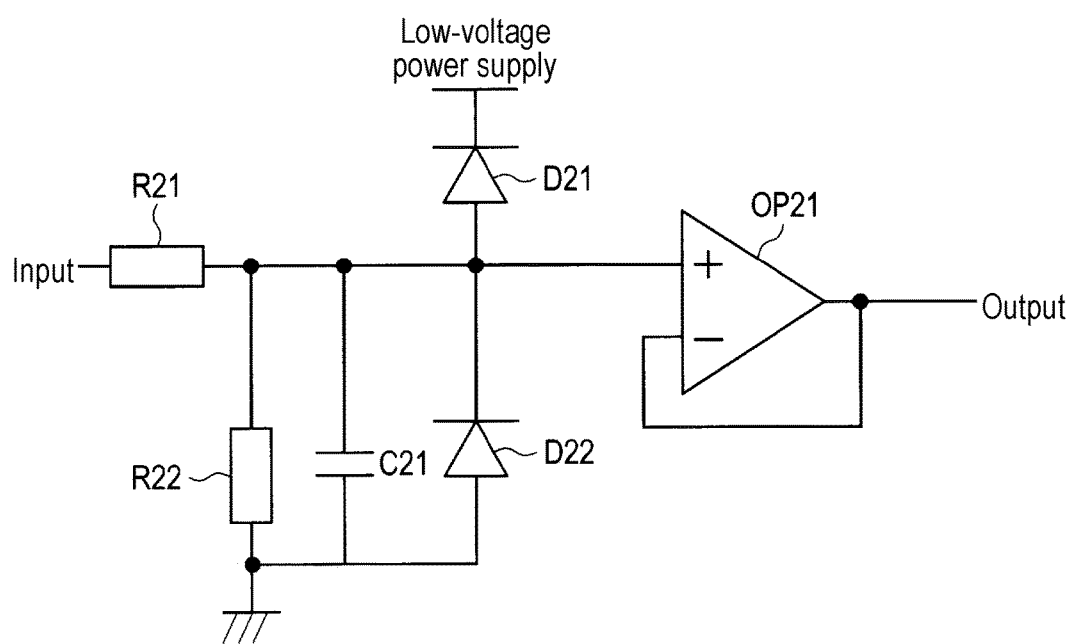
FIG. 7 is a circuit diagram of a specific example of a buffer circuit shown in FIG. 6.

FIG. 6 is a configuration diagram of abnormality detection device 10 B according to a third embodiment. FIG. 7 is a circuit diagram of a specific example of buffer circuit 24 shown in FIG. 6. The configuration of abnormality detection device 10B is different from that according to the first embodiment in that abnormality detection device 10B includes buffer circuit 24. The same configuration elements as those according to the first embodiment are designated by the same numerals and symbols as those in the first embodiment, and their detailed explanations are omitted.

Abnormality detection device 10 B includes signal extraction unit 12B that includes buffer circuit 24. Signal extraction unit 12B includes: first low-pass filter 21, second low-pass filter 22, differential amplifier 23, and buffer circuit 24.

Buffer circuit 24 receives a signal from node n1, and output a signal to both first low-pass filter 21 and second low-pass filter 22. The input impedance of buffer circuit 24 is so high that buffer circuit 24 outputs the thus-received inspection signal to the next circuit-stage with small voltage drop.

Moreover, buffer circuit 24 has the following function. That is, when low- and high-frequency noises inputted from high-voltage circuit 100 have excessively high amplitudes, buffer circuit 24 suppresses their amplitudes. Specifically, as shown in FIG. 7, buffer circuit 24 includes: negative-feedback operational amplifier OP21, input resistor R21, voltage-dividing resistor R22, by-pass capacitor C21, and protection diodes D21 and D22. One end of input resistor R21 is coupled with the input terminal, and the other end is coupled with a non-inverting input terminal of operational amplifier OP21. Protection diode D21 is connected between a voltage power supply and the non-inverting input terminal of operational amplifier OP21. Protection diode D22 is connected between the ground and the non-inverting input terminal of operational amplifier OP21. Voltage-dividing resistor R22 is connected between the ground and the non-inverting input terminal of operational amplifier OP21. By-pass capacitor C21 is connected between the ground and the non-inverting input terminal of operational amplifier OP21. Alternatively, each of voltage-dividing resistor R22 and by-pass capacitor C21 may be connected to, instead of the ground, either a first offset voltage output or a second offset voltage output.

With this configuration, when low-frequency noises having large amplitudes are inputted to buffer circuit 24, the amplitudes of the noises are reduced through use of input resistor R21 and voltage-dividing resistor R22. Moreover, when high-frequency noises having large amplitudes are inputted to buffer circuit 24, the amplitudes of the noises are reduced through use of input resistor R21 and by-pass capacitor C21. With these operations, even when low- or high-frequency noises having excessively high amplitudes are inputted, the amplitude of the signal to which the inspection signal is added can be reduced to within a dynamic range of operational amplifier OP21 for buffering.

With such buffer circuit 24, the inspection signal output to node n1 can be output to both first low-pass filter 21 and second low-pass filter 22, with a small voltage drop. Moreover, with such buffer circuit 24, even when low- or high-frequency noises having excessively high amplitudes are inputted from high-voltage circuit 100, the inspection signal can be output, without being clipped off, to both first low-pass filter 21 and second low-pass filter 22.

The other operations are the same as those of abnormality detection device 10 described in the first embodiment.

As described above, in accordance with abnormality detection device 10B, the following advantageous effects can be achieved in addition to the advantageous effects of the first embodiment. That is, buffer circuit 24 allows signal extraction unit 12B to extract the inspection signal with higher sensitivity. Moreover, buffer circuit 24 has the function of reducing the low- or high-frequency noises. This allows the prevention of the inspection signal from being clipped off at the stages prior to signal input unit 13, even when buffer circuit 24 is disposed.

Up to this point, each of the embodiments of the present invention has been described.

Note that, in the above embodiments, signal extraction unit 12 includes first low-pass filter 21. However, in the case where the occurrence of high-frequency noises is rather low, first low-pass filter 21 may be omitted. Moreover, first low-pass filter 21 may be disposed between nodes n1 and n2 (see FIG. 2). Node n2 is a branching point at which the signal path of the inspection signal is branched to a signal path passing through second low-pass filter 22 and a signal path not passing through second low-pass filter 22.

Moreover, in the embodiments described above, signal input unit 13 receiving the extraction signal determines the presence of abnormality of insulation resistance 111, based on the level of the extraction signal. However, a controller is separately disposed for determining the presence of abnormality. Then, the controller determines the presence of abnormality of insulation resistance 111 based on the level of the extraction signal which is received by signal input unit 13.

INDUSTRIAL APPLICABILITY

The present invention can be applied to abnormality detection devices for detecting the presence or absence of abnormalities of insulation resistance of high-voltage circuits that are mounted to vehicles, for example.

What is claimed is:

1. An abnormality detection device comprising:
a coupling capacitor including:
    a first end; and
    a second end to be coupled with a high-voltage circuit;
a signal output unit which outputs an alternating-current inspection signal, the signal output unit being coupled with the first end of the coupling capacitor via a detection resistor;
a signal extraction unit which extracts the inspection signal as an extraction signal, the inspection signal being output between the detection resistor and the coupling capacitor; and
a signal input unit which receives the extraction signal and detects an abnormality of insulation resistance of the high-voltage circuit based on a level of the received extraction signal,
wherein the signal extraction unit includes:
    a signal removing filter which removes a signal equal in frequency to the inspection signal, and passes, through the signal removing filter, a low-frequency noise lower in frequency than the inspection signal; and
    a subtraction circuit which outputs a differential signal as the extraction signal, the differential signal being a difference between a signal having been passed through the signal removing filter and a signal not having been passed through the signal removing filter, and
wherein the signal removing filter is a low-pass filter which removes the signal equal in frequency to the inspection signal and passes the low-frequency noise through the signal removing filter.

2. The abnormality detection device according to claim 1,
wherein the signal extraction unit further includes a noise removing filter which removes a high-frequency noise higher in frequency than the inspection signal and passes, through the noise removing filter, the low-frequency noise and the signal equal in frequency to the inspection signal, and
the subtraction circuit outputs a differential signal as the extraction signal, the differential signal being a difference between the signal having been passed through the signal removing filter, and a signal that having been passed through the noise removing filter but having not been passed through the signal removing filter.

3. An abnormality detection device comprising:
a coupling capacitor including:
   a first end; and
   a second end to be coupled with a high-voltage circuit;
a signal output unit which outputs an alternating-current inspection signal, the signal output unit being coupled with the first end of the coupling capacitor via a detection resistor;
a signal extraction unit which extracts the inspection signal as an extraction signal, the inspection signal being output between the detection resistor and the coupling capacitor; and
a signal input unit which receives the extraction signal and detects an abnormality of insulation resistance of the high-voltage circuit based on a level of the received extraction signal,
wherein the signal extraction unit includes:
   a signal removing filter which removes a signal equal in frequency to the inspection signal, and passes, through the signal removing filter, a low-frequency noise lower in frequency than the inspection signal; and
   a subtraction circuit which outputs a differential signal as the extraction signal, the differential signal being a difference between a signal having been passed through the signal removing filter and a signal not having been passed through the signal removing filter,
wherein the signal extraction unit further includes a noise removing filter which removes a high-frequency noise higher in frequency than the inspection signal and passes, through the noise removing filter, the low-frequency noise and the signal equal in frequency to the inspection signal, and
wherein the subtraction circuit outputs a differential signal as the extraction signal, the differential signal being a difference between the signal having been passed through the signal removing filter, and a signal that having been passed through the noise removing filter but having not been passed through the signal removing filter.

4. The abnormality detection device according to claim 3, wherein the noise removing filter is a low-pass filter which removes the high-frequency noise higher in frequency than the inspection signal and passes, through the noise removing filter, the low-frequency noise and the signal equal in frequency to the inspection signal.

* * * * *